United States Patent
Tian et al.

(10) Patent No.: US 12,174,153 B2
(45) Date of Patent: Dec. 24, 2024

(54) METHOD FOR ESTIMATING CONTRIBUTION RATE OF ELASTIC ENERGY OF TOP PLATE DURING INSTABILITY CATASTROPHE OF DEEP GAS-CONTAINING COAL BODY

(71) Applicant: SHANDONG UNIVERSITY OF SCIENCE AND TECHNOLOGY, Qingdao (CN)

(72) Inventors: Chenglin Tian, Qingdao (CN); Qianting Hu, Qingdao (CN); Haitao Sun, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 0 days.

(21) Appl. No.: 18/571,767

(22) PCT Filed: Jan. 9, 2023

(86) PCT No.: PCT/CN2023/071366
§ 371 (c)(1),
(2) Date: Dec. 19, 2023

(87) PCT Pub. No.: WO2023/138430
PCT Pub. Date: Jul. 27, 2023

(65) Prior Publication Data
US 2024/0264054 A1     Aug. 8, 2024

(30) Foreign Application Priority Data

Jan. 20, 2022   (CN) .......................... 202210063522.0

(51) Int. Cl.
*G01N 3/08*       (2006.01)
*G01N 3/06*       (2006.01)
*G01N 33/24*      (2006.01)

(52) U.S. Cl.
CPC .............. *G01N 3/08* (2013.01); *G01N 3/066* (2013.01); *G01N 33/24* (2013.01); *G01N 2203/0067* (2013.01)

(58) Field of Classification Search
None
See application file for complete search history.

(56) References Cited

U.S. PATENT DOCUMENTS

| 2014/0019047 A1* | 1/2014 | Lin ......................... E21F 17/18 702/2 |
| 2015/0000903 A1* | 1/2015 | Ly ....................... G01N 23/2251 382/109 |

(Continued)

FOREIGN PATENT DOCUMENTS

| CN | 101581229 A | * 11/2009 |
| CN | 102243223 A | * 11/2011 |

(Continued)

OTHER PUBLICATIONS

Xiaohan Yang, Coal Burst: A State of the Art on Mechanism and Prevention from Energy Aspect, Apr. 20, 2020 (Year: 2019).*

(Continued)

*Primary Examiner* — Shelby A Turner
*Assistant Examiner* — Brandon J Becker
(74) *Attorney, Agent, or Firm* — Hemisphere Law, PLLC; Zhigang Ma (57) ABSTRACT

The present disclosure discloses a method for estimating a contribution rate of elastic energy of a top plate during instability catastrophe of a deep gas-containing coal body, which specifically includes the following steps: acquiring gas pressure of a coal seam; acquiring a thickness of the coal seam and the top plate according to a borehole histogram; coring in the field, processing and pre-processing coal samples, and acquiring an elastic modulus of the top plate, gas-containing coal and standard specimens of a gas-containing coal-rock combination through indoor mechanical tests, respectively; deducing contribution of the elastic energy of the top plate with the help of a graphic area for a stress-strain curve, and obtaining a quantitative expression of the contribution rate of the elastic energy of the top plate based on the elastic modulus and the thickness of the top plate and the gas-containing coal. According to the present disclosure, the function of the elastic energy of the top plate in coal-rock gas dynamic disasters is taken into full account, and a calculation method and a specific quantitative calculation formula are given, so that the function of the elastic energy of the top plate in disasters can be more clearly understood, and beneficial reference is provided for accurate prevention and control of coal-rock gas dynamic disasters in mines.

5 Claims, 4 Drawing Sheets

(56) References Cited

U.S. PATENT DOCUMENTS

| | | | |
|---|---|---|---|
| 2017/0235016 A1* | 8/2017 | Prioul | G01N 29/04 73/152.01 |
| 2017/0268970 A1* | 9/2017 | Heinlein | G01N 3/08 |
| 2018/0031732 A1* | 2/2018 | Mosse | G01V 20/00 |
| 2021/0263003 A1* | 8/2021 | Wang | G01N 3/08 |

FOREIGN PATENT DOCUMENTS

| | | |
|---|---|---|
| CN | 105866373 A | 8/2016 |
| CN | 110261220 A | 9/2019 |
| CN | 111665135 A | 9/2020 |

OTHER PUBLICATIONS

ISA (CNIPA), ISR of PCT/CN2023/071366, Feb. 22, 2023.

Lai, Xingping et al. "Energy release law during the damage evolution of water-bearing coal and rock and pick-up of AE signals of key pregnancy disasters" Chinese Journal of Rock Mechanics and Engineering vol. 39, No. 03, Mar. 31, 2020 (Mar. 31, 2020).

ISA (CNIPA), Written Opinion for PCT/CN2023/071366, Feb. 22, 2023.

* cited by examiner

METHOD FOR ESTIMATING CONTRIBUTION RATE OF ELASTIC ENERGY OF TOP PLATE DURING INSTABILITY CATASTROPHE OF DEEP GAS-CONTAINING COAL BODY

TECHNICAL FIELD

The present disclosure belongs to the technical field of coal mine safety, and relates to a theoretical calculation method of complex dynamic disasters of coal and rock gas in deep wells, in particular to a method for estimating a contribution rate of elastic energy of a top plate during instability catastrophe of a deep gas-containing coal body.

BACKGROUND

China is the largest producer and consumer of coal in the world, and coal plays an important role in the energy structure of China. Although a series of corresponding prevention and control measures have been taken, mine dynamic disasters involving coal and rock gas still occur. In the final analysis, the understanding of the mechanism of coal and rock gas disasters is not clear and perfect enough.

At present, the research on mine dynamic disasters (coal and gas outburst, rock burst) usually focuses on the role of coal itself and gas. On the one hand, the related research conducts analysis only based on the stress and gas situation of the coal seam and directly ignores the elastic energy of the top plate. On the other hand, a rough estimate is only given, but in fact, there are few specific quantitative studies on the elastic energy of the top plate, especially under deep mining conditions. The problems of high ground stress, high temperature and high gas in deep mining increase the risk of coal and gas outburst and the coal and rock impact, which further increases the probability of complex coal and rock dynamic disasters in some high-gas mines and coal and gas outburst mines. Such disasters not only show some characteristics of coal and gas outburst, but also some characteristics of rock burst. The two dynamic disasters coexist, influence and compound with each other. At the same time, the deep composite coal and rock dynamic disaster is a complex mechanical process under the dual effects of "high stress (ground stress) and dynamic disturbance (depressurized mining)". Many factors are intertwined in the process of disaster occurrence, which may lead to mutual inducement, mutual reinforcement or "resonance" effect in the process of accident preparation, occurrence and development. Thus, the mechanism of composite dynamic disasters is more complicated. It is more important to clarify the specific participation role of elastic energy of the top plate in the process of disasters.

SUMMARY

Aiming at the shortcomings of the prior art, the present disclosure provides a method for estimating a contribution rate of elastic energy of a top plate during instability catastrophe of a deep gas-containing coal body. Based on this method, the energy contribution rate of the top plate can be acquired, and the calculation method is simple and easy to operate.

A method for estimating a contribution rate of elastic energy of a top plate during instability catastrophe of a deep gas-containing coal body is provided, including the following steps:

Step 1, acquiring a gas pressure p, a thickness $h_C$ and a top plate thickness $h_R$ of a gas-containing coal seam, respectively;

Step 2, coring the gas-containing coal seam and the top plate, respectively, processing the gas-containing coal seam and the top plate into a cylindrical or rectangular standard specimen, and obtaining an elastic modulus $E_R$ of the top plate and an elastic modulus $E_C$ of the coal seam under the influence of the gas pressure p through mechanical tests; wherein the mechanical test method includes: drilling a hole in a center of a bottom surface of the prepared standard coal sample specimen, wherein the drilled hole has a set depth of 3-5 mm and a diameter of 1-2 mm; embedding an inverted T-shaped gas injection kit into the drilled hole at the bottom of the coal sample specimen and sealing the hole, sealing a contact surface between the bottom of the coal sample specimen and the gas injection kit at the same time, thereafter, placing the specimen into a high-pressure sealed cavity, vacuumizing the specimen, filling gas with a pressure of p, adsorbing and balancing the gas, using a rigid testing machine to load at a set loading rate until the coal sample specimen is destroyed, recording a stress and a strain of the coal sample specimen synchronously, and obtaining the elastic modulus of the coal seam by dividing the stress by the strain;

Step 3, preparing and pre-processing a standard specimen of a coal-rock combination; wherein the specific operations includes: processing pure coal and pure rock specimens according to a coal-rock height ratio and polishing the surfaces of the specimens; drilling a hole in a center of a bottom surface of each coal specimen, wherein the drilled hole has a set depth of 3-5 mm and a diameter of 1-2 mm, embedding an inverted T-shaped gas injection kit into the drilled hole at the bottom of the coal sample specimen and sealing the hole, sealing a contact surface between the bottom of the coal sample specimen and the gas injection kit at the same time; sticking an ultra-thin transparent polyethylene film on the bottom surface of each rock specimen, and sticking three groups of strain gauges at equal intervals on a middle part of a side surface of each rock specimen; bonding the bottom surface of the rock stuck with the ultra-thin transparent polyethylene film and the upper end surface of the coal specimen into a whole with strong glue; and evenly coating 705 #silica gel on the side surface and the upper end surface of the prepared standard specimen of the coal-rock combination and drying the silica gel for later use;

Step 4, carrying out mechanical tests on the prepared standard specimen of the coal-rock combination under the gas pressure p, wherein the specific test method includes: placing the specimen prepared in Step 3 into a high-pressure sealed cavity, vacuumizing the specimen, filling gas with a pressure of p, adsorbing and balancing the gas, using a rigid testing machine to load at a set loading rate until the specimen is destroyed, and recording a stress and a strain of the whole standard specimen of the combination and a strain of the rock in the standard specimen of the combination synchronously; and acquiring the elastic modulus $E_Z$ of the standard specimen of the combination, a first stress-strain curve of the rock and a second stress-strain curve of the standard specimen of the combination, respectively, where $h_R$ and $h_C$, $E_R$ and $E_C$, $E_Z$ and $E_R$ satisfy the relationship (I):

$$h_R = mh_C \quad (I)$$

$$E_R = nE_C$$

$$E_Z = \lambda(m+1)/(m+n)E_R$$

in Formula (I), m>0 and n>0, λ is a correction coefficient, and 0<λ≤1;

Step 5, drawing the first stress-strain curve and the second stress-strain curve in the same coordinate system to analyze and estimate the contribution rate Q of the elastic energy of the top plate, the specific estimation method is as follows:

sub-step 5.1, calculating the elastic energy released by the coal-rock combination;

in the second stress-strain curve of the standard specimen of the combination, taking the corresponding point of a peak value of the combination as a start point released by the elastic energy of the combination, taking the corresponding point of a residual intensity of the combination as an end point released by the elastic energy of the combination, drawing a straight line I parallel to the elastic modulus of the combination through the start point, drawing a straight line II perpendicular to a horizontal axis through the start point, and drawing a straight line III parallel to the horizontal axis and intersecting with the first stress-strain curve through the end point, wherein the area surrounded by the straight lines I, II and III is the elastic energy released by the combination;

sub-step 5.2, calculating the elastic energy released by the top plate;

drawing a straight line parallel to the horizontal axis through a corresponding point of the peak value of the combination to be intersected with the first stress-strain curve of the rock, in which an intersection point is the start point released by the elastic energy of the top plate; drawing a straight line parallel to the horizontal axis through a corresponding point of the residual intensity of the combination to be intersected with the first stress-strain curve of the rock, in which an intersection point is the end point released by the elastic energy of the top plate; drawing a straight line IV parallel to the elastic energy of the top plate through the start point released by the elastic energy of the top plate; drawing a straight line V perpendicular to the horizontal axis through the start point released by the elastic energy of the top plate, wherein the area surrounded by the straight lines III, IV and V is the elastic energy released by the top plate;

sub-step 5.3, estimating the contribution rate of the elastic energy of the top plate;

the ratio of the elastic energy released by the top plate to the elastic energy released by the combination is the contribution rate β of the elastic energy of the top plate;

Step 6, a quantitative expression of the contribution rate of the elastic energy of the top plate: according to the estimation method in Step 5 and in combination with Formula (I), obtaining the expression of the contribution rate β of the elastic energy of the top plate:

$$\beta = \lambda m/(m+n) \quad (II)$$

Formula (II) is the contribution rate of the elastic energy of the top plate during instability catastrophe of the deep gas-containing coal body which is obtained by estimation.

The present disclosure has the following beneficial effects.

1) According to the actual situation on site, the present disclosure provides a method for estimating a contribution rate of elastic energy of a top plate during instability catastrophe of a deep gas-containing coal body, which is a beneficial supplement to the energy of coal and rock gas dynamic disasters, and also provides data support for further clarification the mechanism of breeding and inducing dynamic disasters in the theoretical aspect.

2) According to the present disclosure, the contribution rate of the energy of the top plate can be acquired respectively by calculating the relevant mechanical indexes of the top plate rock, the gas-containing coal and the coal-rock combination, and the calculation method is simple and easy to operate.

3) The present disclosure fully considers the influence of the elastic energy of the top plate for coal and rock gas dynamic disasters, which has important theoretical significance and practical engineering value, and has positive significance for the prediction and prevention of mine complex dynamic disasters such as rock burst-coal and gas outburst induced by deep mining.

BRIEF DESCRIPTION OF THE DRAWINGS

In the figures, 1. First stress-strain curve, 2. Second stress-strain curve, 3. Straight line I, 4. Straight line II, 5. Straight line III, 6. Straight line IV, 7. Straight line V.

DETAILED DESCRIPTION OF THE EMBODIMENTS

In order to fully embody the characteristics and advantages of the present disclosure, the present disclosure will be described in detail with the attached drawings and specific embodiments hereinafter.

Figure 1:
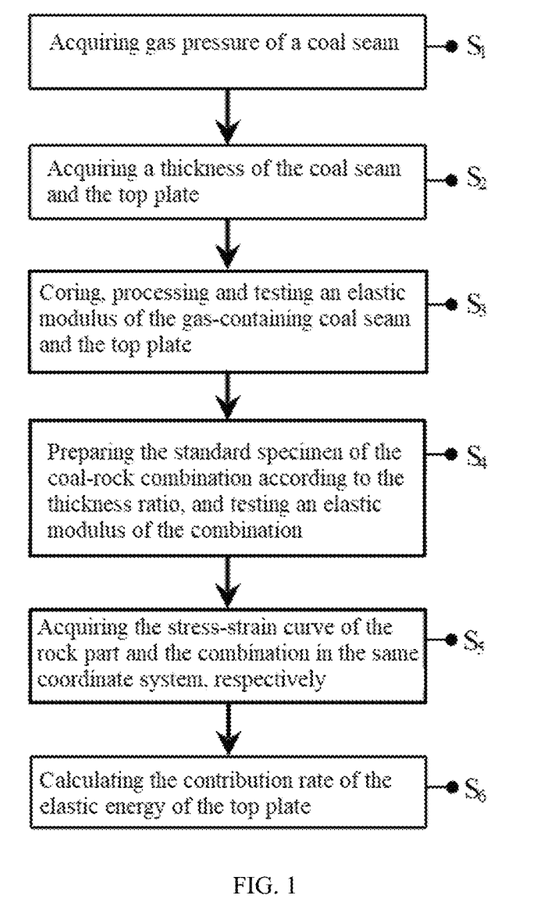
FIG. 1 is a flow chart of a method for estimating a contribution rate of elastic energy of a top plate during instability catastrophe of a deep gas-containing coal body.
Figure 2:
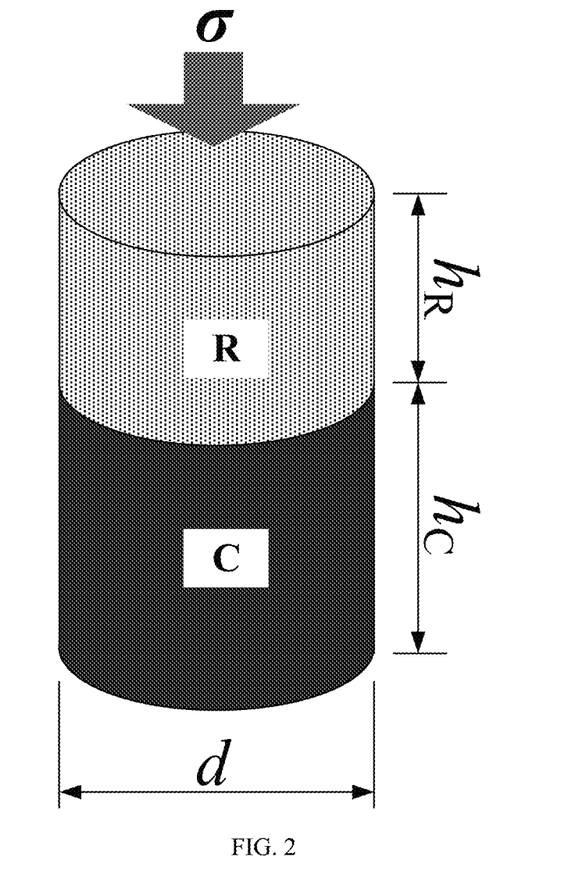
FIG. 2 is a schematic diagram of a coal-rock two-body model according to the present disclosure.
Figure 4:
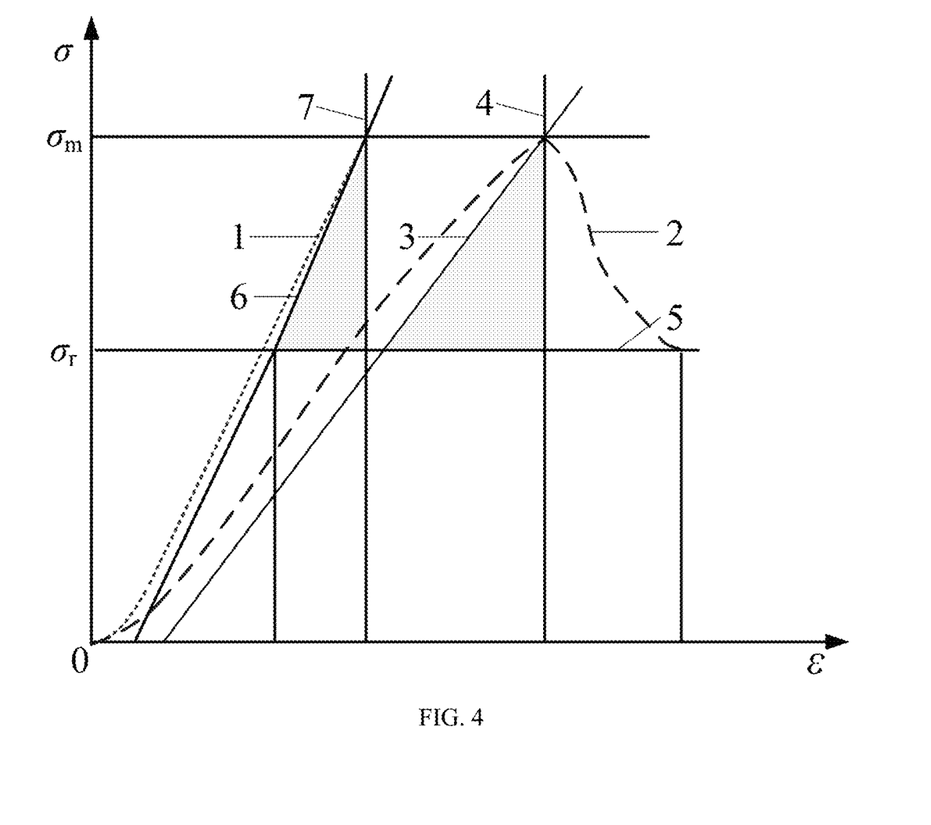
FIG. 4 is a schematic diagram of calculating elastic energy of a top plate and coal-rock combination according to the present disclosure.

As shown in FIG. 1 and FIG. 2, a method for estimating a contribution rate of elastic energy of a top plate during instability catastrophe of a deep gas-containing coal body is provided, including the following steps:

Step 1 $S_1$, acquiring a gas pressure p, a thickness $h_C$ and a top plate thickness $h_R$ of a gas-containing coal seam, respectively;

Step 2 $S_2$, coring the gas-containing coal seam and the top plate, respectively, processing the gas-containing coal seam and the top plate into a cylindrical or rectangular standard specimen, and obtaining an elastic modulus $E_R$ of the top plate and an elastic modulus $E_C$ of the coal seam under the influence of the gas pressure p through mechanical tests; wherein the specific test method of the mechanical tests includes: drilling a hole in a center of a bottom surface of the prepared standard coal sample specimen, wherein the drilled hole has a set depth of 3-5 mm and a diameter of 1-2 mm; embedding an inverted T-shaped gas injection kit into the drilled hole at the bottom of the coal sample specimen and sealing the hole, sealing a contact surface between the bottom of the coal sample specimen and the gas injection kit at the same time, thereafter, placing the specimen into a high-pressure sealed cavity, vacuumizing the specimen, filling gas with a pressure of p, adsorbing and balancing the gas, using a rigid testing machine to load at a set loading rate until the coal sample specimen is destroyed, recording a stress and a strain of the coal sample specimen synchronously;

Step 3 $S_3$, preparing and pre-processing a standard specimen of a coal-rock combination; wherein the specific operations includes: processing pure coal and pure rock specimens according to a coal-rock height ratio and polishing the surfaces of the specimens; drilling a hole in a center of a bottom surface of each coal specimen, wherein the drilled hole has a set depth of 3-5 mm and a diameter of 1-2 mm, embedding an inverted T-shaped gas injection kit into the drilled hole at the bottom of the coal sample specimen and sealing the hole, sealing a contact surface between the bottom of the coal sample specimen and the gas injection kit at the same time; sticking an ultra-thin transparent polyethylene film on the bottom surface of each rock specimen, and sticking three groups of strain gauges at equal intervals on a middle part of a side surface of each rock specimen; bonding the bottom surface of the rock stuck with the ultra-thin transparent polyethylene film and the upper end surface of the coal specimen into a whole with strong glue; and evenly coating 705 #silica gel on the side surface and the upper end surface of the prepared standard specimen of the coal-rock combination and drying the silica gel for later use;

Step 4 $S_4$, carrying out mechanical tests on the prepared standard specimen of the coal-rock combination under the gas pressure p, wherein the specific test method includes: placing the specimen prepared in Step 3 into a high-pressure sealed cavity, vacuumizing the specimen, filling gas with a pressure of p, adsorbing and balancing the gas, using a rigid testing machine to load at a set loading rate until the specimen is destroyed, and recording a stress and a strain of the whole standard specimen of the combination and a strain of the rock in the standard specimen of the combination synchronously; and acquiring the elastic modulus $E_Z$ of the standard specimen of the combination, a first stress-strain curve 1 of the rock and a second stress-strain curve 2 of the standard specimen of the combination through mechanical tests, respectively, where $h_R$ and $h_C$, $E_R$ and $E_C$, $E_Z$ and $E_R$ satisfy the relationship (I):

$$h_R = mh_C \quad (I)$$
$$E_R = nE_C$$
$$E_Z = \lambda(m+1)/(m+n)E_R$$

in Formula (I), m>0 and n>0, $\lambda$ is a correction coefficient, and 0<$\lambda$≤1;

Step 5 $S_5$, drawing the first stress-strain curve 1 and the second stress-strain curve 2 in the same coordinate system to analyze and estimate the contribution rate β of the elastic energy of the top plate, the specific estimation method is as follows:

sub-step 5.1, calculating the elastic energy released by the coal-rock combination;

as shown in FIG. 4, in the second stress-strain curve 2 of the standard specimen of the combination, taking the corresponding point of a peak value of the combination as a start point released by the elastic energy of the combination, taking the corresponding point of a residual intensity of the combination as an end point released by the elastic energy of the combination, drawing a straight line I 3 parallel to the elastic modulus of the combination through the start point, drawing a straight line II 4 perpendicular to a horizontal axis through the start point, and drawing a straight line III 5 parallel to the horizontal axis and intersecting with the first stress-strain curve 1 through the end point, wherein the area surrounded by the straight lines I 3, II 4 and III 5 is the elastic energy released by the combination;

sub-step 5.2, calculating the elastic energy released by the top plate;

drawing a straight line parallel to the horizontal axis through a corresponding point of the peak value of the combination to be intersected with the first stress-strain curve 1 of the rock, in which an intersection point is the start point released by the elastic energy of the top plate; drawing a straight line parallel to the horizontal axis through a corresponding point of the residual intensity of the combination to be intersected with the first stress-strain curve 1 of the rock, in which an intersection point is the end point released by the elastic energy of the top plate; drawing a straight line IV parallel to the elastic energy of the top plate through the start point released by the elastic energy of the top plate; drawing a straight line V 7 perpendicular to the horizontal axis through the start point released by the elastic energy of the top plate, wherein the area surrounded by the straight lines III 5, IV 6 and V 7 is the elastic energy released by the top plate;

sub-step 5.3, estimating the contribution rate of the elastic energy of the top plate;

the ratio of the elastic energy released by the top plate to the elastic energy released by the combination is the contribution rate β of the elastic energy of the top plate.

The detailed derivation process is as follows. It is assumed that the following conditions are satisfied at the same time: (1) only the coal body part is destroyed and the rock part remains relatively intact without obvious cracks on the surface when the standard specimen of the combination is damaged and unstable under the influence of the set gas pressure p; from the point of view of energy dissipation, the rock dissipation energy is only self-dissipation before the peak, and the rest is accumulated elastic strain energy, that is, the rock is in the stage of elastic energy storage before the peak of the combination; (2) based on the analysis of the first stress-strain curve 1 and the second stress-strain curve 2, the accumulation of coal and rock energy at the peak reaches the limit, and the peak and a point after the peak are the turning points from steady damage to unsteady damage of the specimen. After this point, the elastic energy of the rock begins to act on the coal body, accelerating the damage of coal, and the elastic energy really plays a role. The energy action points p and q after the peak are moved to the points m and n of the peak, respectively (point p coincides with point m, and point q coincides with point n), so as to obtain the attached figure as shown in FIG. 4. That is, it is considered that the elastic energy accumulated by the rock starts to act on the coal body at the peak of the combination, that is, the releasing rate of the elastic energy of the top plate is greater than the crack propagation rate in the coal body at the beginning. The lower coal body loses the restraint of the top plate from the peak point, and the elastic energy of the top plate is released and immediately acts on the coal body, thus accelerating the damage of the coal body.

Figure 3:
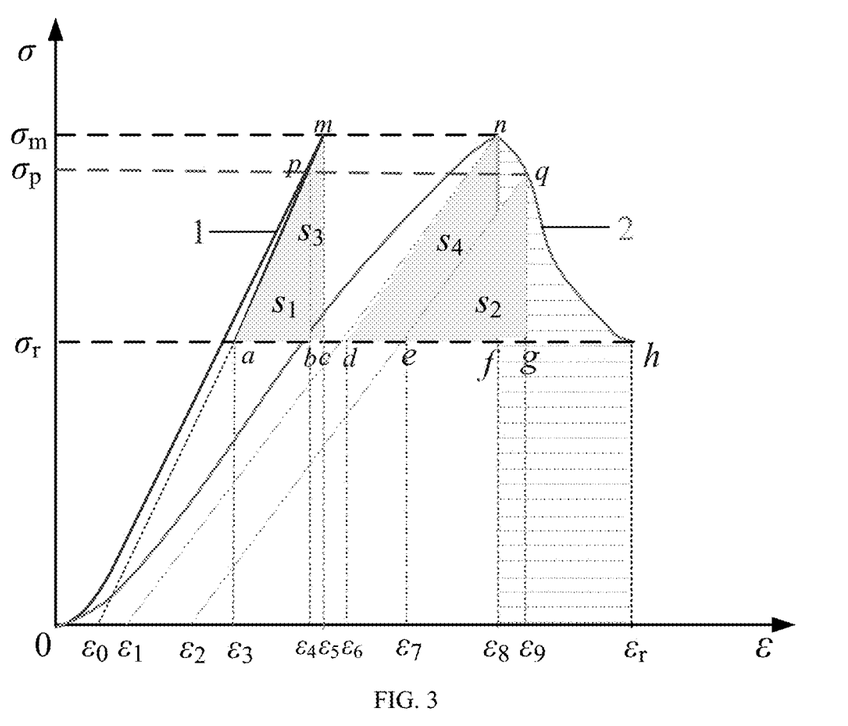
FIG. 3 is an overall schematic diagram of a model for estimating a contribution rate of elastic energy of a top plate according to the present disclosure.

The model for estimating the contribution rate of the elastic energy of the top plate as shown in FIG. 3 is established, in which the standard specimen of the combination has a peak stress of $\sigma_m$ and a peak strain of $\epsilon_8$, and the residual intensity and the residual strain of the standard specimen of the combination are $\sigma_r$ and $\epsilon_r$, respectively; the strain corresponding to the rock part is $\epsilon_5$ when the standard specimen of the combination reaches the peak, the residual strain of the rock part in the standard specimen of the combination after the peak is $\epsilon_3$, and the post-peak intensity $\sigma_p$ is the start point where the elastic energy of the rock can really act on the coal body. At this time, the strains corresponding to the standard specimen of the combination and the rock are $\epsilon_9$ and $\epsilon_4$, respectively. The straight line parallel to the elastic modulus of the rock is drawn through point m (the unloading line-ma passes through point p), which has an intersection point a with the residual stress $\sigma_r$, and the corresponding strain of point a is $\epsilon_3$. The intersection point $\epsilon_0$ with the coordinate axis represents the self-dissipation strain in the loading process of the rock. The straight line parallel to the elastic modulus of the standard specimen of the combination is drawn through point n (the unloading line-nd), which has an intersection point d with the residual stress, and the corresponding strain of point d is $\epsilon_6$. The intersection point $\epsilon_1$ with the coordinate axis represents the self-dissipation strain in the loading process of the standard specimen of the combination. The straight line parallel to the elastic modulus of the standard specimen of the combination is drawn through point q (the unloading line-qe), which has an intersection point e with the residual stress, and the corresponding strain of point e is $\epsilon_7$. The intersection point $\epsilon_2$ with the coordinate axis represents the total dissipation strain of the standard specimen of the combination before instability. The straight lines perpendicular to the coordinate axis are drawn through p, m, n and q, which have intersection points b, c, f and g with the residual stress, respectively. Point h corresponds to the residual stress-residual strain point of the standard specimen of the combination. According to the above analysis, it can be seen that when all elastic energy accumulated by the rock in the standard specimen of the combination acts on the coal body, it is the most dangerous situation, that is, the requirement is satisfied that $\Delta$pab coincides with $\Delta$mac. The vertex is located at point m, that is, $s_1$ coincides with $s_3$. It is assumed that $s_1=s_3=s_R$. Similarly, $\Delta$qeg coincides with $\Delta$ndf. The vertex is located at point n, that is, $s_2$ coincides with $s_4$. Similarly, it is assumed that $s_2=s_4=s_C$. Obviously, the calculated value of the elastic energy of the top plate at this time is the maximum value, no matter whether the value is the total accumulated amount or the amount that really acts on the coal body to accelerate its damage. The contribution rate of the elastic energy of the top plate can be estimated by using this value.

A sixth step $S_6$, according to the estimation method in Step 5 and in combination with Formula (I), a quantitative expression of the contribution rate $\beta$ of the elastic energy of the top plate is obtained. When the combination is damaged, a part of the energy comes from the releasable elastic strain energy accumulated by the coal body itself, and the other part comes from the destructive part of the releasable elastic strain energy accumulated by the rock. Obviously, the more this part, the more pronounced the effect of aggravating the damage of the coal body, and the more severe the damage of the coal body. Therefore, the contribution rate $\beta$ of the elastic energy of the top plate is used to characterize the function of the elastic energy of the rock, where the definition $\beta$ satisfies the following formula:

$$\beta = (s_R/s_C) \times 100\% \quad (2)$$

$$S_R = \int_{\varepsilon_3}^{\varepsilon_5} \sigma d\varepsilon = \frac{E}{2}\varepsilon^2 \Big|_{\varepsilon_3}^{\varepsilon_5} \quad (3)$$

$$\varepsilon_5 = \sigma_m/E_R \quad (4)$$

$$\varepsilon_3 = \sigma_r/E_R \quad (5)$$

In Formula (3), $S_R$ is the elastic energy accumulated by the standard pure rock specimen. Formula (4) and Formula (5) are substituted into Formula (3) so as to obtain:

$$s_R = S_R \cdot \frac{h_R}{h_R + h_C} = \frac{m}{m+1} \cdot \frac{\sigma_m^2 - \sigma_r^2}{2E_R} \quad (6)$$

Similarly:

$$s_C = (\sigma_m^2 - \sigma_r^2)/2E_Z \quad (7)$$

Formula (6) and Formula (7) are substituted into Formula (2) so as to obtain:

$$\beta = \frac{s_R}{s_C} = \frac{E_Z}{E_R} \cdot \frac{m}{m+1} \quad (8)$$

Formula (I) is substituted into Formula (8) so as to obtain:

$$\beta = \lambda m/(m+n) \quad (II)$$

Formula (II) is the expression of the contribution rate of the elastic energy of the top plate during instability catastrophe of the deep gas-containing coal body which is obtained by using the estimation method.

Although the specific embodiment of the present disclosure has been described with the attached drawings, it is not a limitation on the scope of protection of the present disclosure. Those skilled in the art should understand that on the basis of the technical scheme of the present disclosure, various modifications or transformations that can be made by those skilled in the art without creative labor are still within the scope of protection of the present disclosure.

What is claimed is:

1. A method for estimating a contribution rate of elastic energy of a top plate during instability catastrophe of a deep gas-containing coal body, comprising the following steps:
   Step 1, acquiring a gas pressure p, a thickness $h_C$ and a top plate thickness $h_R$ of a gas-containing coal seam, respectively;
   Step 2, coring the gas-containing coal seam and the top plate, respectively, processing the gas-containing coal seam and the top plate into a cylindrical or rectangular standard specimen, and obtaining an elastic modulus $E_R$ of the top plate and an elastic modulus $E_C$ of the coal seam under the influence of the gas pressure p through mechanical tests;

Step 3, preparing and pre-processing a standard specimen of a coal-rock combination;

Step 4, carrying out mechanical tests on the prepared standard specimen of the coal-rock combination under the gas pressure p, and acquiring the elastic modulus $E_Z$ of the standard specimen of the combination, a first stress-strain curve of the rock and a second stress-strain curve of the standard specimen of the combination, respectively, where $h_R$ and $h_C$, $E_R$ and $E_C$, $E_Z$, and $E_R$ satisfy the relationship (I):

$$h_R = mh_C \quad (I)$$
$$E_R = nE_C$$
$$E_Z = \lambda(m+1)/(m+n)E_R$$

in Formula (I), m>0 and n>0, $\lambda$ is a correction coefficient, and 0<$\lambda$≤1;

Step 5, drawing the first stress-strain curve and the second stress-strain curve in the same coordinate system to analyze and estimate the contribution rate $\beta$ of the elastic energy of the top plate, the specific estimation method is as follows:

sub-step 5.1, calculating the elastic energy released by the coal-rock combination;

in the second stress-strain curve of the standard specimen of the combination, taking the corresponding point of a peak value of the combination as a start point released by the elastic energy of the combination, taking the corresponding point of a residual intensity of the combination as an end point released by the elastic energy of the combination, drawing a straight line I parallel to the elastic modulus of the combination through the start point, drawing a straight line II perpendicular to a horizontal axis through the start point, and drawing a straight line III parallel to the horizontal axis and intersecting with the first stress-strain curve through the end point, wherein the area surrounded by the straight lines I, II and III is the elastic energy released by the combination;

sub-step 5.2, calculating the elastic energy released by the top plate;

drawing a straight line parallel to the horizontal axis through a corresponding point of the peak value of the combination to be intersected with the first stress-strain curve of the rock, in which an intersection point is the start point released by the elastic energy of the top plate; drawing a straight line parallel to the horizontal axis through a corresponding point of the residual intensity of the combination to be intersected with the first stress-strain curve of the rock, in which an intersection point is the end point released by the elastic energy of the top plate; drawing a straight line IV parallel to the elastic energy of the top plate through the start point released by the elastic energy of the top plate; drawing a straight line V perpendicular to the horizontal axis through the start point released by the elastic energy of the top plate, wherein the area surrounded by the straight lines III, IV and V is the elastic energy released by the top plate;

sub-step 5.3, estimating the contribution rate of the elastic energy of the top plate;

the ratio of the elastic energy released by the top plate to the elastic energy released by the combination is the contribution rate $\beta$ of the elastic energy of the top plate;

Step 6, according to the estimation method in Step 5 and in combination with Formula (I), obtaining a quantitative expression of the contribution rate $\beta$ of the elastic energy of the top plate:

$$\beta = \lambda m/(m+n) \quad (II)$$

Formula (II) is the contribution rate of the elastic energy of the top plate during instability catastrophe of the deep gas-containing coal body which is obtained by estimation;

wherein the specific test method of obtaining an elastic modulus $E_C$ of the coal seam under the influence of the gas pressure p through mechanical tests in Step 2 comprises: drilling a hole in a center of a bottom surface of the prepared standard coal sample specimen, wherein the drilled hole has a set depth of 3-5 mm and a diameter of 1-2 mm; embedding an inverted T-shaped gas injection kit into the drilled hole at the bottom of the coal sample specimen and sealing the hole, sealing a contact surface between the bottom of the coal sample specimen and the gas injection kit at the same time, thereafter, placing the specimen into a high-pressure sealed cavity, vacuumizing the specimen, filling gas with a pressure of p, adsorbing and balancing the gas, using a rigid testing machine to load at a set loading rate until the coal sample specimen is destroyed, recording a stress and a strain of the coal sample specimen synchronously, and obtaining the elastic modulus of the coal seam by dividing the stress by the strain.

2. The method for estimating the contribution rate of the elastic energy of the top plate during instability catastrophe of the deep gas-containing coal body according to claim 1, wherein preparing and pre-processing a standard specimen of a coal-rock combination in Step 3 specifically comprises: processing pure coal and pure rock specimens according to a coal-rock height ratio and polishing the surfaces of the specimens; drilling a hole in a center of a bottom surface of each coal specimen, wherein the drilled hole has a set depth of 3-5 mm and a diameter of 1-2 mm, embedding an inverted T-shaped gas injection kit into the drilled hole at the bottom of the coal sample specimen and sealing the hole, sealing a contact surface between the bottom of the coal sample specimen and the gas injection kit at the same time; sticking an ultra-thin transparent polyethylene film on the bottom surface of each rock specimen, and sticking three groups of strain gauges at equal intervals on a middle part of a side surface of each rock specimen; bonding the bottom surface of the rock stuck with the ultra-thin transparent polyethylene film and the upper end surface of the coal specimen into a whole with strong glue; and evenly coating 705 #silica gel on the side surface and the upper end surface of the prepared standard specimen of the coal-rock combination and drying the silica gel for later use.

3. He method for estimating the contribution rate of the elastic energy of the top plate during instability catastrophe of the deep gas-containing coal body according to claim 1, wherein the specific test method of carrying out mechanical tests on the prepared standard specimen of the coal-rock combination under the gas pressure p in Step 4 comprises: placing the specimen processed in Step 3 into a high-pressure sealed cavity, vacuumizing the specimen, filling gas with a pressure of p, adsorbing and balancing the gas, using a rigid testing machine to load at a set loading rate until the specimen is destroyed, and recording a stress and a strain of the whole standard specimen of the combination and a strain of the rock in the standard specimen of the combination synchronously.

4. The method for estimating the contribution rate of the elastic energy of the top plate during instability catastrophe of the deep gas-containing coal body according to claim 1, wherein the specific test method of
mechanical tests on the prepared specimen of the coal-rock combination under the gas pressure p in Step 4 comprises: placing the specimen processed in Step 3 Into a high-pressure sealed cavity, vacuumizing the specimen, filling gas with pressure of p, adsorbing and balancing the gas, using a rigid testing machine to load at a set loading rate until the specimen is destroyed, and recording a stress and a strain of the whole standard specimen of the combination and a strain of the rock in the standard specimen of the combination synchronously.

5. The method for estimating the contribution rate of the elastic energy of the top plate during instability catastrophe of the deep gas-containing coal body according to claim 3, wherein the specific test method of carrying out mechanical tests on the prepared standard specimen of the coal-rock combination under the gas pressure p in Step 4 comprises: placing the specimen processed in Step 3 into a high-pressure sealed cavity, vacuumizing the specimen, filling gas with a pressure of p, adsorbing and balancing the gas, using a rigid testing machine to load at a set loading rate until the specimen is destroyed, and recording a stress and a strain of the whole standard specimen of the combination and a strain of the rock in the standard specimen of the combination synchronously.

* * * * *